United States Patent
Kim et al.

(10) Patent No.: US 9,828,605 B2
(45) Date of Patent: Nov. 28, 2017

(54) COMPOSITION FOR ENHANCING RADIATION SENSITIVITY COMPRISING PI4K ISOZYME INHIBITOR

(71) Applicant: Seoul National University R&DB Foundation, Seoul (KR)

(72) Inventors: In ah Kim, Seongnam-si (KR); Dan Hyo Kim, Goseong-gun (KR); Jean ny Kwon, Seoul (KR); Ji Min Park, Yongin-si (KR); Young hee Park, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 0 days.

(21) Appl. No.: 15/048,872

(22) Filed: Feb. 19, 2016

(65) Prior Publication Data

US 2017/0051289 A1    Feb. 23, 2017

(30) Foreign Application Priority Data

Apr. 22, 2015    (KR) ........................ 10-2015-0056653

(51) Int. Cl.
*A61K 31/4709* (2006.01)
*C12N 15/113* (2010.01)
*C07H 21/02* (2006.01)

(52) U.S. Cl.
CPC ...... *C12N 15/1137* (2013.01); *A61K 31/4709* (2013.01); *C12N 2310/14* (2013.01); *C12N 2320/31* (2013.01)

(58) Field of Classification Search
None
See application file for complete search history.

(56) References Cited

U.S. PATENT DOCUMENTS

2015/0051199 A1*  2/2015  Woodhead ........... C07D 213/73
                                                           514/230.5

OTHER PUBLICATIONS

Martin et al., Journal of Gastroenterology, Pancreatology & Liver Disorders vol. 1(4):1-4, 2014.*
Berger, et al., Roles for Endocytic Trafficking and Phosphatidylinositol 4-Kinase III Alpha in Hepatitis C Virus Replication, PNAS Early Edition, 2009, 1-6.
Bianco, et al., Metabolism of Phosphatidylinositol 4-Kinase IIIα-Dependent PI4P Is Subverted by HCV and Is Targeted by a 4-Anilino Quinazoline with Antiviral Activity, PloS Pathogens, 2012, 8:3:1-17.
Illboudo, et al., Overexpression of Phosphatidylinositol 4-Kinase Type IIIα Is Associated With Undifferentiated Status and Poor Prognosis of Human Hepatocellular Carcinoma, BMC Cancer 2014, 14:7:1-8.
Ishikawa, et al., Identification of Genes Related to Invasion and Metastasis in Pancreatic Cancer by cDNA Representational Difference Analysis, J. Exp. Clin. Cancer Res., 2003, 22:2:299-306.
Kim, et al., Preferential Radiosensitization of 9L Glioma Cells Transduced With HSV-tk Gene by Acyclovir, Journal of Neuro-Oncology, 1997, 33:189-194.
Li, et al., PI4KIIα Is a Novel Regulator of Tumor Growth by Its Action on Angiogenesis and HIF-1α regulation, Oncogene, 2010, 29:2550-2559.
Smith, et al., Chapter 17, Chemo- and Radiosensitization Through Inhibition of PI3K/Akt Signaling, Cancer Drug Discovery and Development: Apoptosis, Senescence and Cancer, $2^{nd}$ Ed., edited by D. Gewirtz et al., p. 313-334.

* cited by examiner

*Primary Examiner* — Sean McGarry
(74) *Attorney, Agent, or Firm* — Blank Rome LLP

(57) ABSTRACT

The present disclosure relates to a composition for enhancing radiation sensitivity including a PI4K isozyme inhibitor as an active ingredient. As the PI4K isozyme inhibitor, a PI4K isozyme-specific siRNA or antiviral agent according to the present disclosure has an excellent effect of enhancing radiation sensitivity such as reducing viability of the cancer cells and radiation resistance during in radiation irradiation and suppressing and delaying DNA damage repair induced by the radiation by inhibiting the PI4K isozyme to be used as a radiation sensitivity adjuvant and an anticancer treatment assisting agent.

5 Claims, 9 Drawing Sheets

(A) U251

(B) BT-474

COMPOSITION FOR ENHANCING RADIATION SENSITIVITY COMPRISING PI4K ISOZYME INHIBITOR

CROSS-REFERENCE TO RELATED APPLICATIONS

This application is based on and claims priority from Korean Patent Application No. 10-2015-0056653, filed on Apr. 22, 2015, with the Korean Intellectual Property Office, the disclosure of which is incorporated herein in its entirety by reference.

TECHNICAL FIELD

The present disclosure relates to a composition for enhancing radiation sensitivity including a PI4K isozyme inhibitor as an active ingredient.

BACKGROUND

A cancer treatment method may be largely divided into surgery, radiotherapy, and chemotherapy, and currently, in Korea, the number of cancer patients receiving the radiotherapy has increased every year and thus, the importance of the radiotherapy in the cancer treatment has also increased.

The radiotherapy is known as an essential treatment method in various kinds of cancers, but it has been pointed out as problems in that radiation resistance of the cancer cells is obtained and efficiency in the radiotherapy is deteriorated by the damage to normal tissues in radiotherapy with a high radiation dose. Accordingly, researches on a radiation sensitizer for enhancing efficiency of the radiotherapy have been attempted, but the radiation sensitizers which have been reported until the present are mainly anticancer agents, and for example, taxol, cisplatin, and the like have been reported.

Further, a radiotherapy enhancer which has no property as an anticancer and is used only in the radiotherapy is tirapazamine, but it is known that the tirapazamine has an effect on only hypoxic tumor cells and has a marginal effect on clinical radiotherapy because drug delivery to the inside of the tumor tissue is in adequate due to tumor-specific internal pressure in hypoxia.

However, when the anticancer agents used for enhancing the radiotherapy effect is combined with the radiotherapy, toxicity of the anticancer agents may be complicatedly shown with side effects shown in the radiotherapy, that is, inflammation of the radiotherapy site, gastroenteric trouble, nausea, vomiting, and diarrhea. Particularly, cancers in the central nervous system are caused from other cell series including glia such as astrocytes and oligodendrocytes. Astrocytic tumor (astrocytomas) may be divided into diffuse astrocytoma and localized astrocytoma according to an interaction with adjacent microenvironments. The localized astrocytoma has proliferation having a clear interface with the ambient microenvironment and limited potential infiltration, while the diffuse astrocytoma has a characteristic of cellular infiltration far away from peritumoral margin and a main tumor formation site regardless of a tumor grade. The diffuse astrocytoma is classified into three types of astrocytoma (World Health Organization [WHO] grade), anaplastic astrocytoma (WHO grade), and glioblastoma multiform (GBM, WHO grade). The diffuse astrocytoma having the three grades has an infiltration characteristic, and particularly, glioma (GBM) has characteristics of higher proliferation, necrosis and hypoxia, angiogenesis, high infiltration to a support structure of the brain, and high cancer recurrence rate. Since transition to other tissues is easy, various attempts for enhancing cancer treatment efficiency thereof have been conducted, but there is a problem in that there is a limitation only in the chemotherapy, and even in the radiotherapy, the cancer cells are not treated well by obtaining radiation resistance.

Further, in the brain tumor treatment, the radiotherapy in addition to surgical treatment and chemotherapy is an important treatment method. Among the brain tumors, in GBM brain tumor patients as the WHO grade, prognosis (cancer recurrence) is not good and an average survival rate is one year and a 5-year survival rate is less than 5% in spite of surgical therapy, chemotherapy, radiotherapy, or complicated therapy (e.g. radiotherapy and chemotherapy or surgical therapy and radiotherapy). Among the brain tumor treatment methods, the radiotherapy is a method of removing abnormal cells by delaying a cell cycle (DNA damage checkpoint) or inducing apoptosis with respect to the DNA damage caused by the radiation. However, there are problems of the radiotherapy in that radiation-resistive cancer cells cause recurrence of the cancer due to inherent radiation resistance of the cancer cells and an increase in resistance according to the radiotherapy and radiation-resistive cells have resistance to the anticancer agents.

Accordingly, development of radiation sensitivity enhancers capable of minimizing side effects and optimizing radiotherapy while enhancing the radiation sensitivity to the cancer cells having inherent radiation resistance has been urgently required.

Meanwhile, phosphoinositide (PI) of a cell membrane regulates various cell functions such as cell proliferation, receptor signal transduction, cytoskeletal rearrangement, and motility. In the human cells, phosphatidylinositol 4-phosphate (PI4P) is generated by a phosphatidylinositol 4 kinase (PI4K), and the PI4K has II$\alpha$, II$\beta$, III$\alpha$, and III$\beta$ as four isozymes. The PI4P generated by the PI4K is a required substance for two types of PI-dependent signaling systems, that is, a phospholipase C (PLC)-PKC signaling system and a phosphoinositide 3-kinase (PI3K)-Akt signaling system which regulate cell proliferation and movement. Accordingly, propagation of the PI4P is interrupted through inhibition of the PI4K to become a useful treatment strategy capable of simultaneously inhibiting PLC and PI3K signal transduction in the reception activation signal process.

Over the last 20 years, in the cancers, a role of the PI3K signaling is very actively verified to be highlighted as a major target of the anticancer treatment together with discovery of phosphatase and tensin homolog (PTEN), and various drugs are developed and clinically implemented, while the role of the PI4K in the cancer does not receive proper attention.

Recently, based on universities and research institutes in United States and England, while the above research results that the PI4K plays an important role in occurrence of specific cancers start to be reported, attempts to investigate new roles of PI4K in occurrence, progression, and treatment of the cancer are being reviewed, but mostly remain in a barren state as an initial stage of the researches.

Meanwhile, it is known that 4-anilino quinazoline as a replication inhibitor of hepatitis C virus has no mechanism which is clearly found, but has an antiviral effect by targeting a virus protein NS5A. Recently, it is reported that PI4K-III$\alpha$ is a host factor for replication of the hepatitis C virus, and a research on a mechanism that AL-9 as one of a 4-anilino quinazoline compound inhibits the PI4K-III$\alpha$ to have an antiviral effect is reported.

Direct-acting antiviral agents (DAA) are drugs which directly act to HCV virus, and availability and stability thereof have already been verified through clinical experiments. Particularly, as compared with peginterferon alpha and ribavirin which have been used as standard therapy to the hepatitis C virus, in spite of side effects of hardness, a similar or excellent therapeutic response is reported and included in care recommendations in the liver academy in US and Europe.

As a result, the inventors conducted researches for developing a new composition for enhancing radiation sensitivity and verified that PI4K isozyme-specific siRNA and antiviral agent as PI4K isozyme inhibitors are treated to have an excellent effect of enhancing radiation sensitivity such as reducing viability of the cancer cells and radiation resistance during in radiation irradiation and suppressing and delaying DNA damage repair induced by the radiation, and completed the present disclosure.

SUMMARY

The present disclosure has been made in an effort to provide a composition for enhancing radiation sensitivity including a PI4K isozyme inhibitor as an active ingredient.

Further, the present disclosure has been made in an effort to provide a composition for assisting anticancer treatment including a PI4K isozyme inhibitor as an active ingredient for enhancing anticancer activity.

An exemplary embodiment of the present disclosure provides a composition for enhancing radiation sensitivity including a PI4K isozyme-specific siRNA or antiviral agent as an active ingredient.

Another exemplary embodiment of the present disclosure provides a pharmaceutical composition for assisting anticancer treatment including a PI4K isozyme-specific siRNA or antiviral agent as an active agent for enhancing anticancer activity.

Yet another exemplary embodiment of the present disclosure provides a food composition for assisting anticancer treatment including a PI4K isozyme-specific siRNA or antiviral agent as an active agent for enhancing anticancer activity.

According to the exemplary embodiment of the present disclosure, the PI4K isozyme-specific siRNA or antiviral agent has an excellent effect of enhancing radiation sensitivity such as reducing viability of the cancer cells and radiation resistance during in radiation irradiation and suppressing and delaying DNA damage repair induced by the radiation by inhibiting the PI4K isozyme to be usefully used as a radiation sensitivity adjuvant and an anticancer treatment assisting agent.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
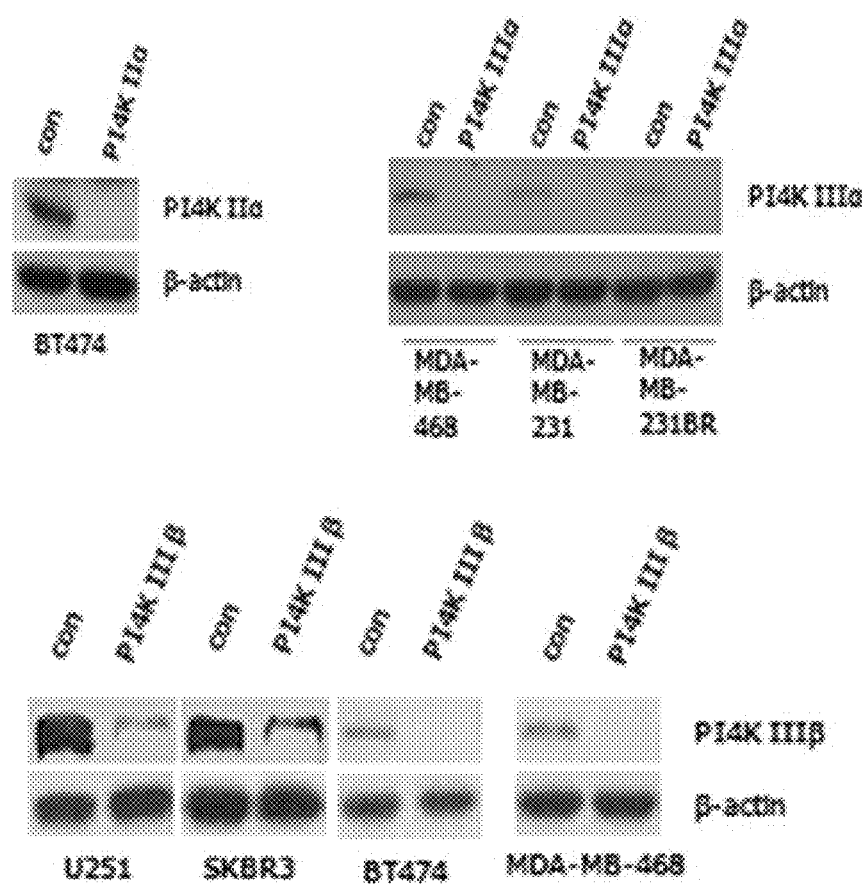
FIG. 1 is a diagram verifying transformation after impregnating siRNA to a brain tumor cell line U-251 and breast cancer cell lines BT-474, SKBR 3, MDA-MB-468, MDA-MB-231, and MDA-MB-231BR through immune blotting.

In the following detailed description, reference is made to the accompanying drawing, which forms a part hereof. The illustrative embodiments described in the detailed description, drawing, and claims are not meant to be limiting. Other embodiments may be utilized, and other changes may be made, without departing from the spirit or scope of the subject matter presented here.

The present disclosure provides a composition for enhancing radiation sensitivity including phosphatidylinositol 4 kinase (PI4K) isozyme inhibitor as an active ingredient.

Hereinafter, the present disclosure will be described in detail.

The present disclosure includes a PI4K isozyme-specific siRNA or antiviral agent as the PI4K isozyme inhibitor.

The PI4K isozyme of the present disclosure may be PI4KIIα or PI4KIIIα.

Small RNA (sRNA) is largely classified into microRNA (miRNA) and small interfering RNA (siRNA) according to a generated method, as ribonucleic acid having a length of about 17 to 25 nucleotides which serves to regulate gene expression in vivo. The siRNA is derived from long double strand RNA (hereinafter, referred to as "dsRNA") and is sRNA which is specifically bound to mRNA having a complementary sequence to inhibit protein expression.

The siRNA of the present disclosure may be directly chemically synthesized or may be synthesized by various methods known in the art, such as a synthesizing method using in-vitro transcription (Brummelkamp T R, et al., 2002, A system for stable expression of short interfering RNAs in mammalian cells, Science 296: 550-553).

The siRNA of the present disclosure may be a form in which RNA having two strands makes a pair to form double strand siRNA, and may be a form which is modified as a structure having a short hairpin to be used for transfection by using a plasmid-based shRNA vector, a PCR expression cassette, and the like.

The PI4K isozyme-specific siRNA as an active ingredient of the present disclosure targets the PI4K isozyme to inhibit expression of the PI4K isozyme.

The PI4K isozyme-specific siRNA may be derived from mammals and for example, may be derived from monkeys, pigs, horses, cattle, sheep, dogs, cats, mice, and rabbits and preferably, human.

The siRNA of the present disclosure is a PI4K isozyme-specific siRNA including a sense strand including any one sequence selected from SEQ ID NOS: 1 to 16 and an antisense strand including the complementary sequence thereof, and the sense strand or the antisense strand of the siRNA may include at least one chemical modification.

The antiviral agent of the present disclosure may be simeprevir, sofosbuvir, daclatasvir, ribavirin, sedipasvir, telaprevir, boceprevir, asunaprevir, or danoprevir, and preferably, simeprevir represented by the following Formula 1, as direct-acting antiviral agents (DAA), which are being developed or used as hepatitis C virus treating agents.

[Formula 1]

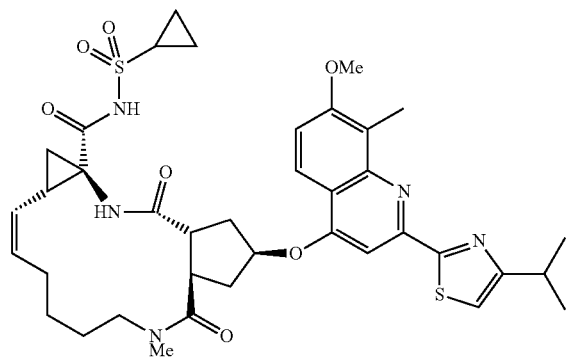

The antiviral agent inhibits the PI4K isozyme which is a host factor in the replication of hepatitis C virus.

A cancer-cell death pathway is classified into cancer-cell apoptosis (programmed cell death type I) and cancer-cell autophagy (programmed cell death type II) pathways. The PI4K isozyme-specific siRNA or antiviral agent according to the present disclosure has an effect of enhancing radiation sensitivity such as reducing viability of the cancer cells and radiation resistance during in radiation irradiation and suppressing and delaying DNA damage repair induced by the radiation by inhibiting the PI4K isozyme.

The "radiation resistance" of the present disclosure means that abnormal cells are not died or slightly died in spite of radiation irradiation in disease treatment using radiation. Alternatively, in the radiation treatment, there is no treatment effect from the initial treatment or initially, there is the disease treatment effect, but the treatment effect is lost in the continuous treatment process.

The "the radiation sensitivity enhancement" of the present disclosure means that the sensitivity of cells to the radiation is enhanced in the radiation treatment. As a result, the radiation treatment efficiency may be increased, and particularly, in the cancer treatment, the radiation sensitivity of tumor cells is enhanced to have a tumoricidal effect and a growth inhibiting effect of the radiation on the tumor cells.

The "radiation treatment" of the present disclosure includes irradiating the radiation after administrating the composition of the present disclosure to the cancer cells, and the "radiation irradiation" may mean ionizing radiation, particularly, gamma radiation irradiated by linear accelerators or radionuclides which are generally used. The radiation irradiation by the radionuclides may be externally or internally performed, and the amount of the administrated siRNA or antiviral agent, a radiation dosage, and intermittence of the radiation dosage may vary according to a series of variables such as types and locations of the tumor and patient's response to chemotherapy or radiotherapy.

Further, as a technique for the radiation irradiation of the present disclosure, brachytherapy, radionuclide therapy, external beam radiotherapy, hyperthermia (including cryoablation therapy and hyperthermia therapy), radiosurgery, charge-particle radiotherapy, neutron radiotherapy, photodynamic therapy, and the like may be included.

The radiation sensitivity enhancement and the radiotherapy of the present disclosure may be applied to any animal in which the cancer may be caused, and the animal includes livestock such as cattle, pigs, sheep, horse, dog, and cat as well as the human and primates.

As described above, the PI4K isozyme-specific siRNA or antiviral agent according to the present disclosure has an excellent radiation sensitivity enhancement effect to be used as a medicine or a sanitary aid used for the radiation sensitivity enhancement.

Further, the present disclosure provides a method of enhancing radiation sensitivity including administrating a PI4K isozyme-specific siRNA or hepatitis C virus treating agent to a subject.

The PI4K isozyme may be PI4KIIα or PI4KIIIα.

The siRNA may include a sense strand including any one sequence selected from SEQ ID NOS: 1 to 16 and the complementary antisense strand thereof.

The hepatitis C virus treating agent may be simeprevir, sofosbuvir, daclatasvir, ribavirin, sedipasvir, telaprevir, boceprevir, asunaprevir, or danoprevir, and preferably, simeprevir represented by the following Formula 1, as direct-acting antiviral agents (DAA).

[Formula 1]

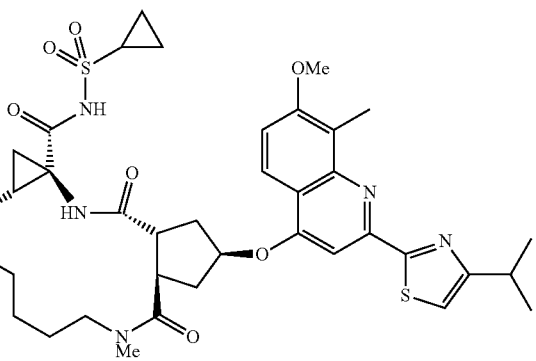

Further, the present disclosure provides a composition for assisting anticancer treatment including a PI4K isozyme-specific siRNA or antiviral agent as an active agent for enhancing anticancer activity.

The composition includes a pharmaceutical composition or a food composition.

The PI4K isozyme-specific siRNA or antiviral agent enhances radiation sensitivity to be used for anticancer treatment using radiation and may enhance efficiency of the anticancer treatment to be used for assisting the anticancer treatment.

The cancer is not limited and may be lung cancer, bone cancer, pancreatic cancer, skin cancer, oral cancer, pharynx cancer, uterine cancer, ovarian cancer, rectal cancer, stomach cancer, breast cancer, endometrial carcinoma, cervical carcinoma, vaginal carcinoma, small intestine cancer, thyroid cancer, parathyroid cancer, prostate cancer, chronic or acute leukemia, lymphocytic lymphoma, bladder cancer, kidney cancer, liver cancer, colon cancer, or brain tumor, and preferably brain tumor or breast cancer.

The brain tumor includes primary and metastatic brain tumor and malignant brain tumor, and includes neuroglioma, astrocytoma, glioblastoma, medulloblastoma, meningioma, acoustic neurinoma, pituitary tumor, lymphoma, and the like. Preferably, the brain tumor may be neuroglioma.

The breast cancer also includes primary and metastatic breast cancer and malignant breast cancer, and includes ductal carcinoma in situ, invasive duct carcinoma, invasive acinar carcinoma, mucous carcinoma, medullary carcinoma, papillary carcinoma, coronary carcinoma, and the like. Preferably, the breast cancer may be invasive duct carcinoma.

The composition of the present disclosure may further include a carrier, an excipient, and a diluent which are properly and generally used in preparation of the pharmaceutical composition. Further, the composition of the present disclosure may be formulated and used in forms, such as an oral formulation such as a powder, a granule, a tablet, a capsule, a suspension, an emulsion, syrup, and an aerosol, an external preparation, a suppository, and a sterile injection solution. It is preferred that a proper medicine which is known in the art uses a medicine disclosed in the document (Remington's Pharmaceutical Science, recently, Mack Publishing Company, Easton Pa.). The carrier, the excipient, and the diluent which may be included in the composition may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, and the like. When the composition is formulated, the formulation may be prepared by using a diluent or an excipient, such as filler, an extender, a binder, a wetting agent, a disintegrating agent, and a surfactant which are generally used. A solid formulation for oral administration includes a tablet, a pill, a powder, a granule, a capsule, and the like, and the solid formulation may be prepared by mixing at least one excipient, for example, starch, calcium carbonate, sucrose or lactose, gelatin, and the like with the composition. Further, lubricants such as magnesium stearate and talc may be used in addition to simple excipients. A liquid formulation for oral administration may use a suspension, a solution, an emulsion, a syrup, and the like, and may include various excipients, for example, a wetting agent, a sweetener, an aromatic agent, a preserving agent, and the like in addition to water and liquid paraffin as simple diluents which are commonly used. A formulation for parenteral administration includes a sterile aqueous solution, a non-aqueous solution, a suspension, an emulsion, and a lyophilizing agent, and a suppository. As the non-aqueous solution and the suspension, propylene glycol, polyethylene glycol, a vegetable oil such as an olive oil, injectable ester such as ethyl oleate, and the like may be used. As a matter of the suppository, witepsol, macrogol, Tween 61, cacao butter, laurin, glycerogelatin, and the like may be used.

In the present disclosure, the term "administration" means providing a predetermined composition of the present disclosure to a subject by any proper method.

A preferable administration amount of the pharmaceutical composition of the present disclosure varies according to a state and a weight of the subject, the degree of the disease, a drug form, and administration route and period, but may be properly selected by those skilled in the art. The administration of the composition may be performed once or several times a day.

The pharmaceutical composition of the present disclosure may be administrated to the subject by various routes. All methods for administration may be expected, and for example, may be administered by oral, rectal or intravenous, intramuscular, subcutaneous, intrauterine dura mater, or intracerebroventricular injection.

The composition of the present disclosure may contain one or more kinds of known active ingredients having effects of enhancing radiation sensitivity or assisting anticancer treatment in addition to the PI4K isozyme-specific siRNA or antiviral agent.

The composition of the present disclosure may be used alone or in a combination with methods using surgery, radiotherapy, hormone therapy, chemotherapy, and biological response modifiers for enhancing radiation sensitivity or assisting anticancer treatment.

The composition of the present disclosure may be added to a sanitary aid composition for enhancing radiation sensitivity or assisting anticancer treatment.

In the case of using the composition of the present disclosure as the sanitary aid composition, the composition may be added as it is or may be used together with other sanitary aids or sanitary aid ingredients and may be properly used according to a general method. A mixed amount of active ingredients may be suitably determined according to a use purpose.

In the present disclosure, "health functional foods" mean foods having a biomodulatory function such as prevention or improvement of diseases, bio-defense, immunity, convalescent restoration, and aging suppression, and needs to be harmless to the human body when taken in the long term.

The composition of the present disclosure may be added to health functional foods for enhancing radiation sensitivity or assisting anticancer treatment. In the case of using the PI4K isozyme-specific siRNA or antiviral agent of the present disclosure as a food additive, the PI4K isozyme-specific siRNA or antiviral agent may be added as it is or may be used together with other sanitary aids or sanitary aid ingredients, and may be properly used according to a general method. The mixed amount of the active ingredient may be suitably determined according to the purpose of use (prevention, health, or therapeutic treatment). Generally, in preparation of foods or beverages, the PI4K isozyme-specific siRNA or antiviral agent of the present disclosure is added with an amount of 15 wt % or less, preferably, 10 wt % or less with respect to a raw material. However, in the case of long-term administration for health and hygiene or health control, the amount may be the range or less. Since there is no problem in terms of safety, the active ingredient may be used with an amount in the range or more.

The kind of food is not particularly limited. Examples of foods which may be added with the material include meat, sausages, bread, chocolate, candies, snacks, cookies, pizza, Ramen, other noodles, gums, dairy products including ice cream, various soups, beverages, tea, drinks, alcohol drinks, and vitamin complex, and include all health foods in the ordinary acceptation.

The health beverage composition of the present disclosure may include various flavors, natural carbohydrates, or the like as an additional ingredient like general beverages. The aforementioned natural carbohydrates may use natural sweeteners such as monosaccharides such as glucose and fructose, disaccharides such as maltose and sucrose, dextrin and cyclodextrin, synthetic sweeteners such as saccharin and aspartame, and the like. A ratio of the natural carbohydrate is generally about 0.01 to 10 g and preferably about 0.01 to 0.1 g per 100 ml of the composition of the present disclosure.

The composition of the present disclosure may include various nutrients, vitamins, electrolytes, flavoring agents, coloring agents, pectic acid and salt thereof, alginic acid and salt thereof, organic acid, a protective colloidal thickener, a pH adjusting agent, a stabilizer, a preservative, glycerin, alcohol, a carbonic acid agent used in a carbonated drink, and the like, in addition to the ingredients. Besides, the composition of the present disclosure may include pulps for preparing natural fruit juices, fruit juice beverages, and vegetable beverages. The ingredients may be used independently or in combination. Although the ratio of the additives is not critical, generally, the ratio is selected in a range of 0.01 to 0.1 parts by weight per 100 parts by weight of the composition of the present disclosure.

Further, the present disclosure provides a method of assisting anticancer treatment including administrating a PI4K isozyme-specific siRNA or hepatitis C virus treating agent to a subject.

The cancer is not limited and may be lung cancer, bone cancer, pancreatic cancer, skin cancer, oral cancer, pharynx cancer, uterine cancer, ovarian cancer, rectal cancer, stomach cancer, breast cancer, endometrial carcinoma, cervical carcinoma, vaginal carcinoma, small intestine cancer, thyroid cancer, parathyroid cancer, prostate cancer, chronic or acute leukemia, lymphocytic lymphoma, bladder cancer, kidney cancer, liver cancer, colon cancer, or brain tumor, and preferably brain tumor or breast cancer.

Hereinafter, preferable Examples and Experimental Examples will be presented in order to help understanding the present disclosure. However, the following Examples and Experimental Examples are just provided for more easily understanding the present disclosure, and the contents of the present disclosure are not limited by Examples and Experimental Examples.

Example 1. Cell Culture

A brain tumor cell line U-251 and breast cancer cell lines BT-474, SKBR 3, MDA-MB-468, MDA-MB-231, and MDA-MB-231BR were cultured in a thermostatic cell incubator in which a condition of 37° C. and 5% $CO_2$ was kept, by using a dulbecco's modified eagle's medium (DMEM) or a rosewell park memories institute (RPMI) 1640 medium containing 10% fetal bovine serum (FBS) and 1% penicillin-streptomycin.

Example 2. Transformation of Cells

In order to prepare a loss of function model, characteristics of the cells cultured in Example 1 were transformed by using an RNA interference method. 1 to $2 \times 10^5$ cells were planted on a 6-well plate and the next day, an antibiotic-free culture medium was replaced. PI4K isozyme and nonspecific control siRNA were added to a reduced serum medium (OPTIMEM, Life technology) and then penetrated to each cell line by using Lipofectamine RNA iMAX (Invitrogen, Carlsbad, Calif.) according to a protocol of the manufacturer. Thereafter, the cells were verified through immune blotting and the result was illustrated in FIG. 1.

As illustrated in FIG. 1, it was verified that the transformation of the cells was normally achieved to inhibit the expression of each PI4K isozyme.

Example 3. Radiation Irradiation

Radiation with 2, 4, and 6 Gy was irradiated to all of the six cell lines (the brain tumor cell line U-251 and the breast cancer cell lines BT-474, SKBR 3, MDA-MB-468, MDA-MB-231, and MDA-MB-231BR) which were transformed in Example 2 by using a GammacellElite machine (dose rate: 3 Gy/min) using Cs gamma-ray as a source.

Experimental Example 1. Verification of Radiation Sensitivity Enhancement Effect by siRNA In order to prove a correlation between the PI4K isozyme and radiation resistance, the radiation resistance was measured by using clonogenic assays. First, after 48 hours of siRNA transduction of Example 2, the cells were collected and 500 with 0 Gy, 1,000 with 2 Gy, 2,000 with 4 Gy, and 4,000 with 6 Gy cells were cultured on a plate according to a radiation dose. After it was checked that the cells were stably attached to a culture dish, radiation was treated with a radiation dose rate of 2.46 Gy per minute by 4 MV X-ray by using a linear accelerator, and the cells were cultured for about 14 days to 23 days until cell colonies were checked with the naked eye. The formed colonies were fixed with 100% methanol and then dyed with 0.5% crystal violet, and surviving fraction was calculated by counting the number of colonies including at least 50 cells. In the surviving fraction, an average of the number of cell colonies in three wells for each radiation dose was shown according to a linear-quadratic model using Kaleidagraph version 3.51 (Synergy Software, Reading, Pa.), and the result was illustrated in FIG. 2.

Figure 2A:
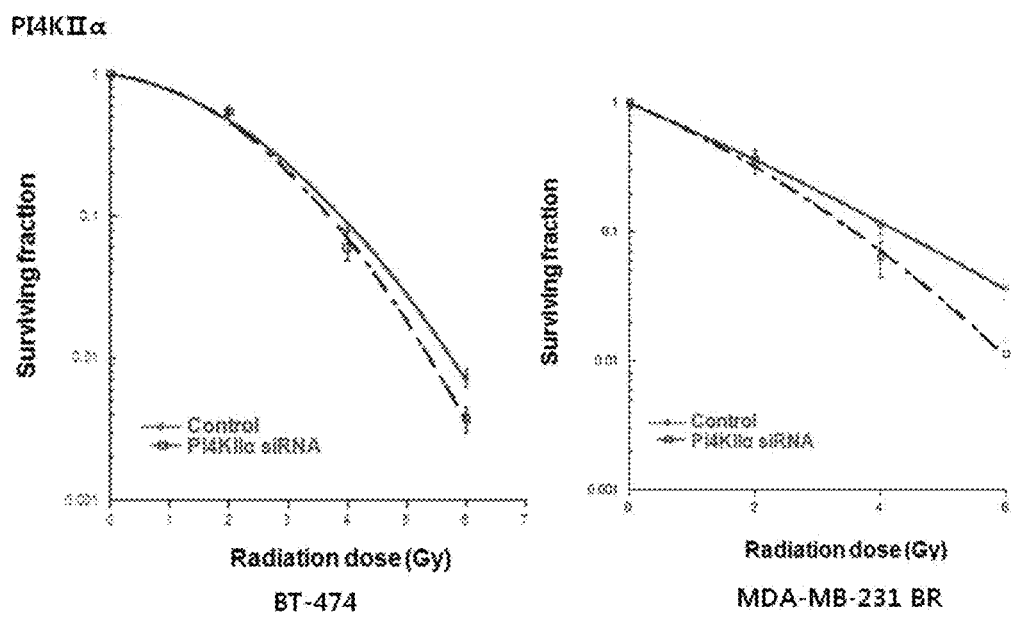
FIG. 2A is a diagram illustrating an effect of enhancing radiation sensitivity when inhibiting PI4KIIα expression using PI4KIIα-siRNA in breast cancer cell lines BT-474 and MDA-MB-231.
Figure 2B:
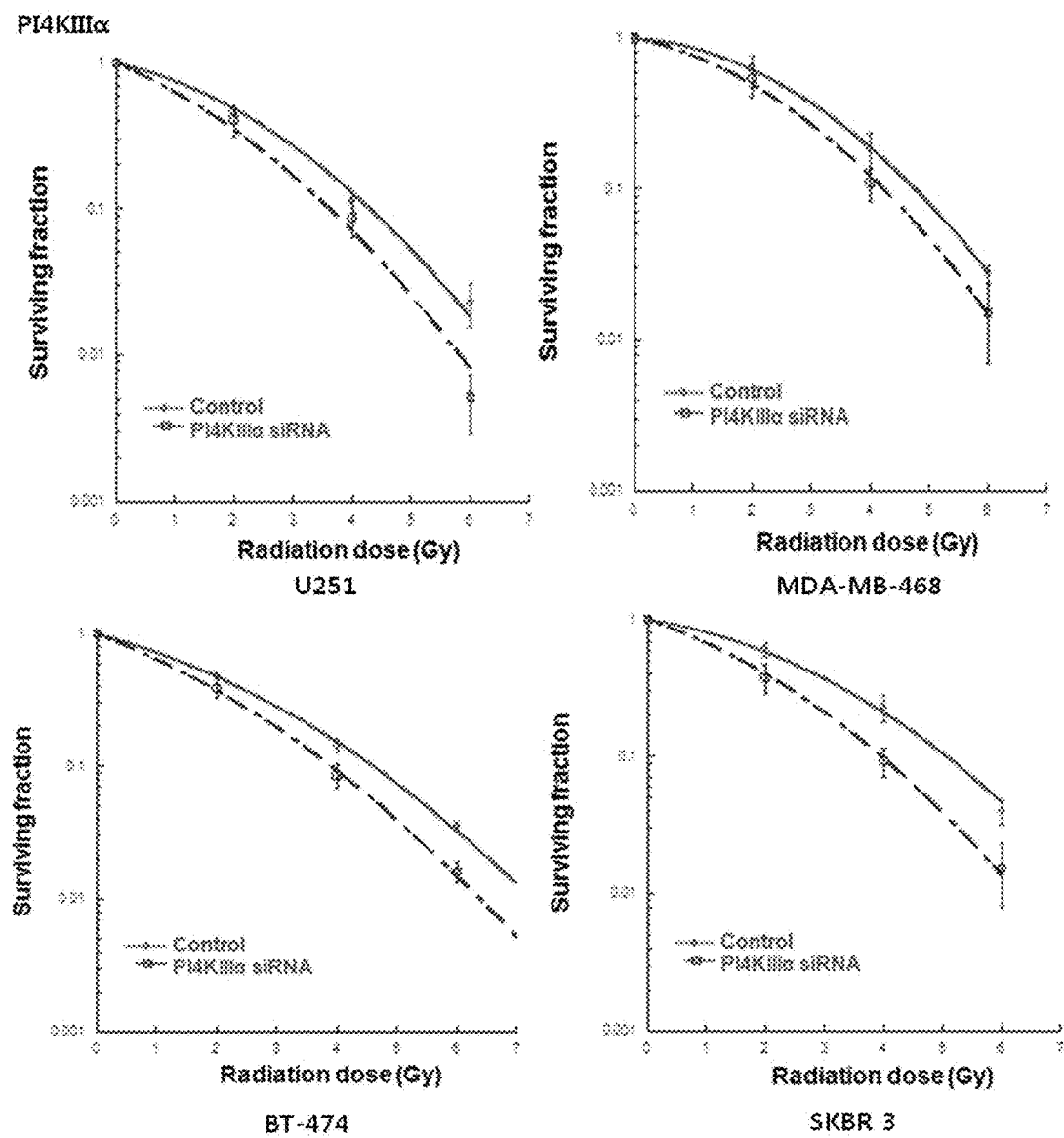
FIG. 2B is a diagram illustrating an effect of enhancing radiation sensitivity when inhibiting PI4KIIα expression using PI4KIIα-siRNA in breast cancer cell lines MDA-MB-468, BT-474, and SKBR3 and a brain tumor cell line U251.

As illustrated in FIG. 2, it was verified that in the breast cancer cell lines BT-474 and MDA-MB-231, the radiation sensitivity was enhanced when inhibiting the expression of PI4KIIα using PI4KIIα-siRNA, and in the breast cancer cell lines BT-474, SKBR3, and MDA-MB-468 and the brain tumor cell line U251, the radiation sensitivity was enhanced when inhibiting the expression of PI4KIIIα using PI4KIIIα-siRNA.

Experimental Example 3. Verification of Effect of siRNA on DNA Damage and Repair Mechanisms In order to verify an effect of a PI4K isozyme on DNA damage and repair mechanisms induced by radiation, a γ-H2AX foci experiment was performed. The six transformed cell lines were divided on a 8-well side glass with $4 \times 10^4$ per well, gamma-ray was irradiated, the cells were fixed to a phosphate buffered saline (PBS) including 4% para-formaldehyde for 20 minutes, and then permeabilization was performed with the PBS containing 0.1% NP-40 for 15 minutes at room temperature. A blocking buffer (PBS+ 0.1% Nail Polish (NP-40)) and 10% bovine serum albumin (BSA) were treated for 30 minutes, and the cells were left for 24 hours at 4° C. with a blocking buffer (1:500) diluted with an anti-γ-H2AX antibody and then left for 2 hours at room temperature with a blocking buffer (1:500) diluted with a fluorescein isothiocyanate (FITC) antibody. Further, in order to show nucleus, the cells were dyed with 4'6-diamidino-2-phenylindole (DAPI) of 100 ng/ml for 5 minutes, a sample was mounted after dyeing and observed by using a LSM 510 microscope (CarlZeiss, Germany), and the result was illustrated in FIG. 3.

Figure 3:
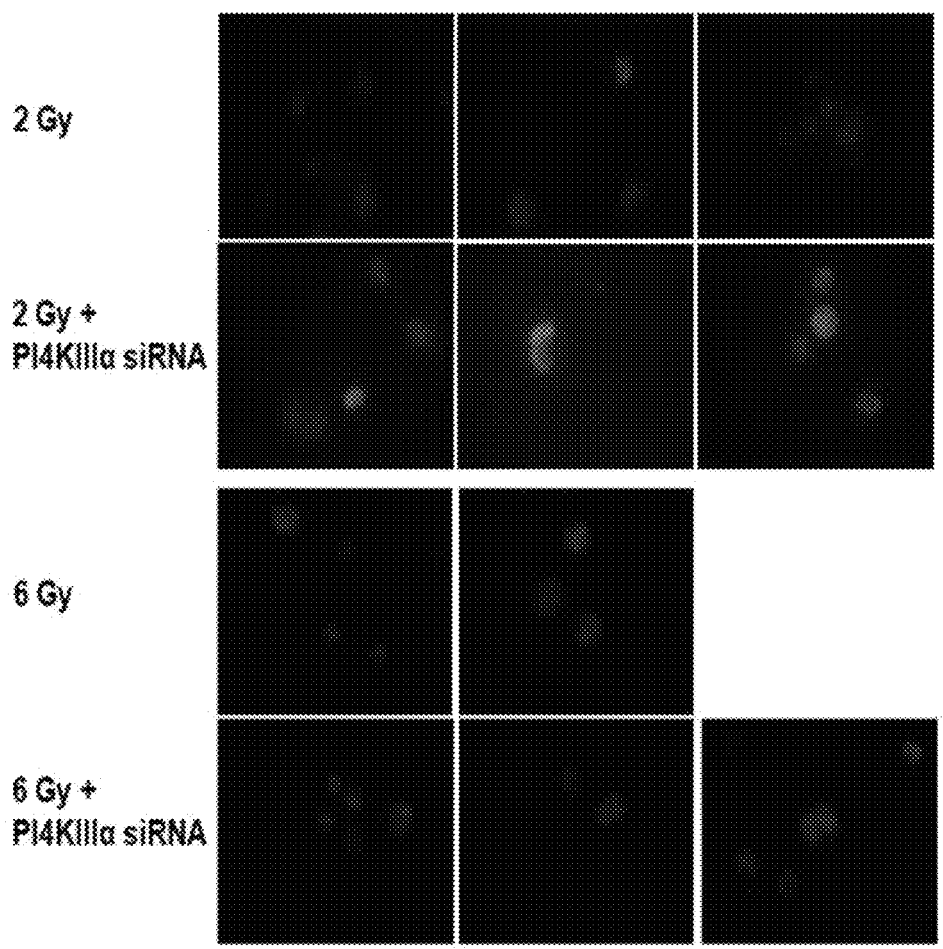
FIG. 3 is a diagram verifying an effect on DNA damage and repair mechanisms when inhibiting PI4K isozyme expression through γ-H2AX foci experiment in SKBR3 cells.

As illustrated in FIG. 3, in the case of the SKBR3 cell line, in a group of inhibiting the PI4KIIIα as compared with a control group, it was verified that relatively many cells were kept in a DNA damage state. It was shown that radiation sensitivity of the SKBR3 cell line was enhanced by inhibiting a repair of the DNA damage induced by radiation of PI4KIIIα-siRNA.

Experimental Example 4. Verification of Radiation Sensitivity Enhancement Effect by Antiviral Agents In order to prove a correlation between the drug treatment and radiation resistance, a colony formation assay was performed. As the hepatitis anti-C virus drug, simeprevir (Olysio) (Janssen Pharmaceutica), sofosbuvir (sovaldi) (Gilead), and daclatasvir (Daklinza) (Bristol-Myers Squibb) were used. In order to determine the use amount thereof, IC50 was verified and illustrated in FIG. 4.

Figure 4:
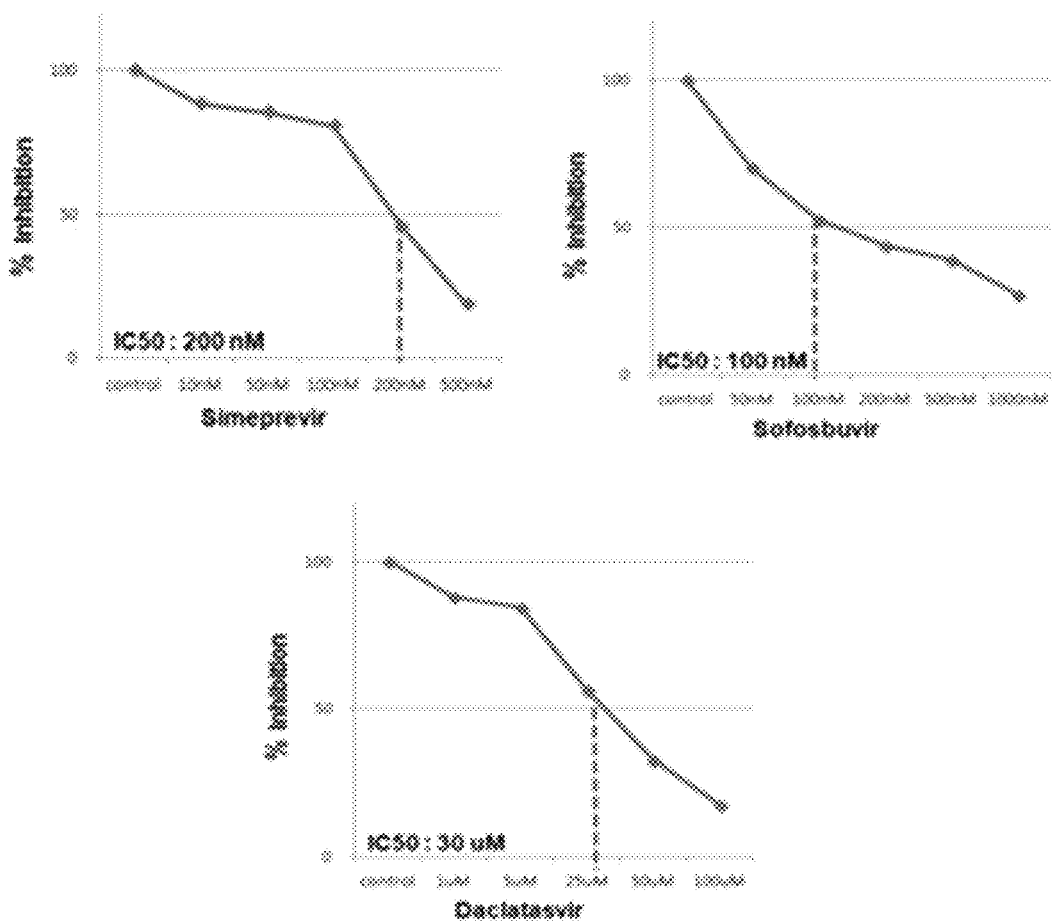
FIG. 4 is a diagram illustrating IC50 for determining used amounts of simeprevir, sofosbuvir, and daclatasvir.

Like IC50 screening data illustrated in FIG. 4, each concentration was determined as 100 nM, 200 nM, and 30 μM.

Figure 5:
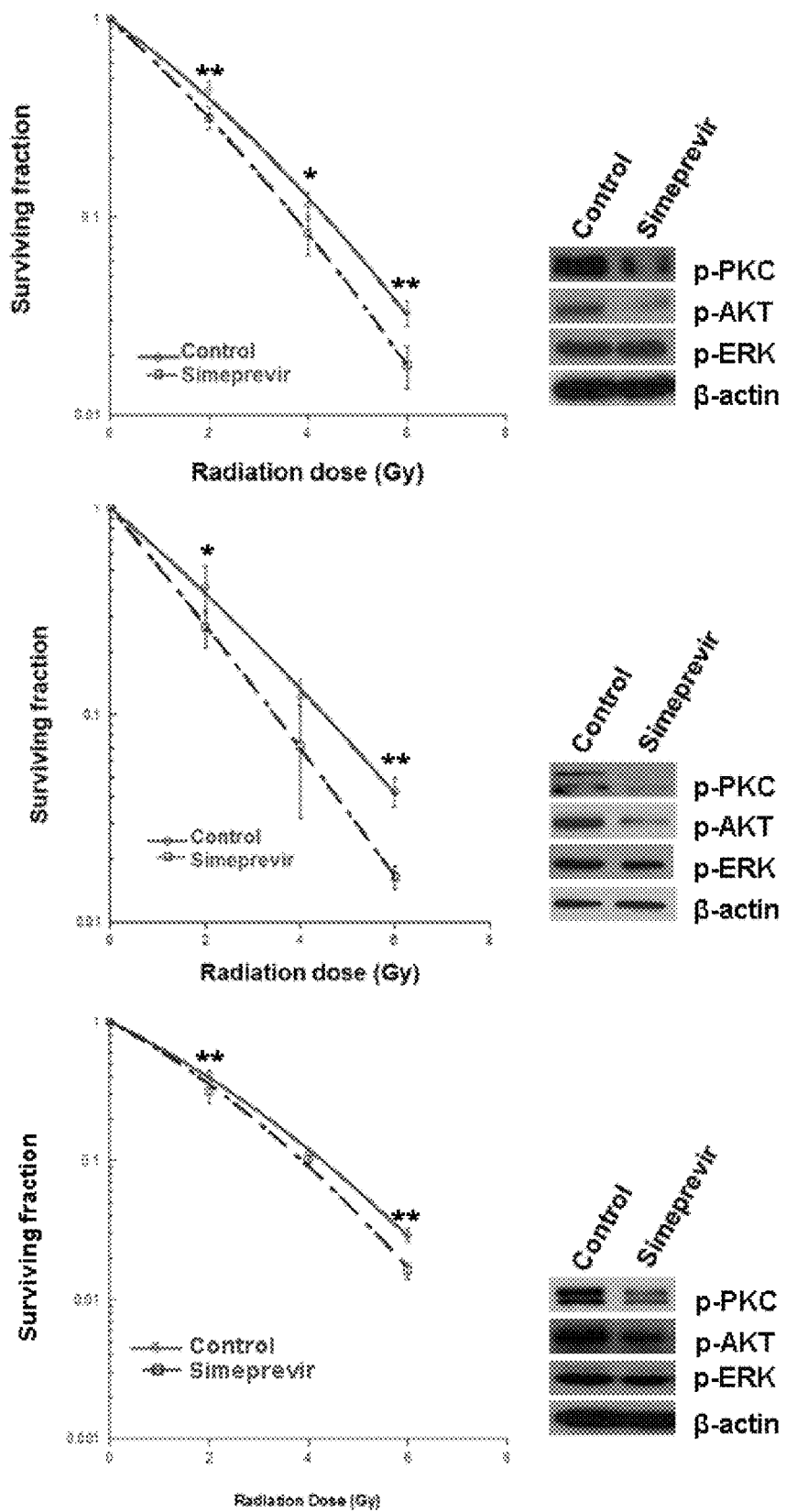
FIG. 5 is a diagram illustrating an effect of enhancing radiation sensitivity when inhibiting PI4K expression using simeprevir (left panel). Also, it shows the phosphorylation degrees of PKCβII, Akt and EPK through immune blotting after treating simeprevir in cancer cells (right panel).
Figure 6:
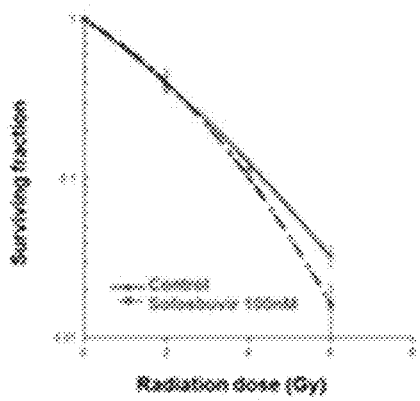
FIG. 6 is a diagram illustrating an effect of enhancing radiation sensitivity when inhibiting PI4K expression using sofosbuvir.
Figure 6:
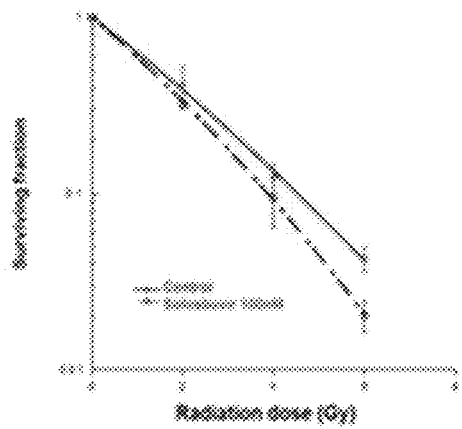
Figure 7:
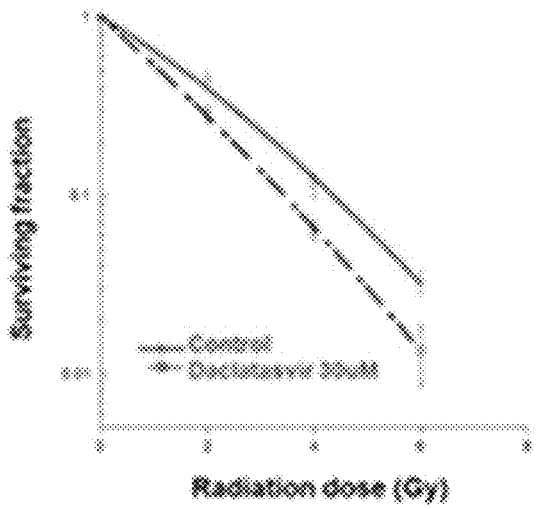
FIG. 7 is a diagram illustrating an effect of enhancing radiation sensitivity when inhibiting PI4K expression using daclatasvir.

After the determined amount of drug was treated in the brain tumor and breast cancer cell lines, the colony formation assay was performed by the same method as Experimental Example 1, and the result was illustrated in FIGS. 5 to 7.

As illustrated in FIGS. 5 and 6, it was verified that the sensitivity to radiation was enhanced in the U251 and BT-474 cell lines by treatment of simeprevir and sofosbuvir, and as illustrated in FIG. 7, it was verified that the sensitivity to radiation was enhanced in the U251 cell line by treatment of daclatasvir.

Simeprevir used as a hepatitis anti-C virus drug was treated and phosphorylation was verified through immune blotting after 24-72 hours of drug treatment. The result was illustrated in FIG. 5 (right panel).

As illustrated in FIG. 5 (right panel), in the U251 cell line, after simeprevir treatment, reduction in phosphorylation of PKC and AKT was verified. Similar results were acquired, and in the BT-474 and HepG2 cell line.

Figure 8:
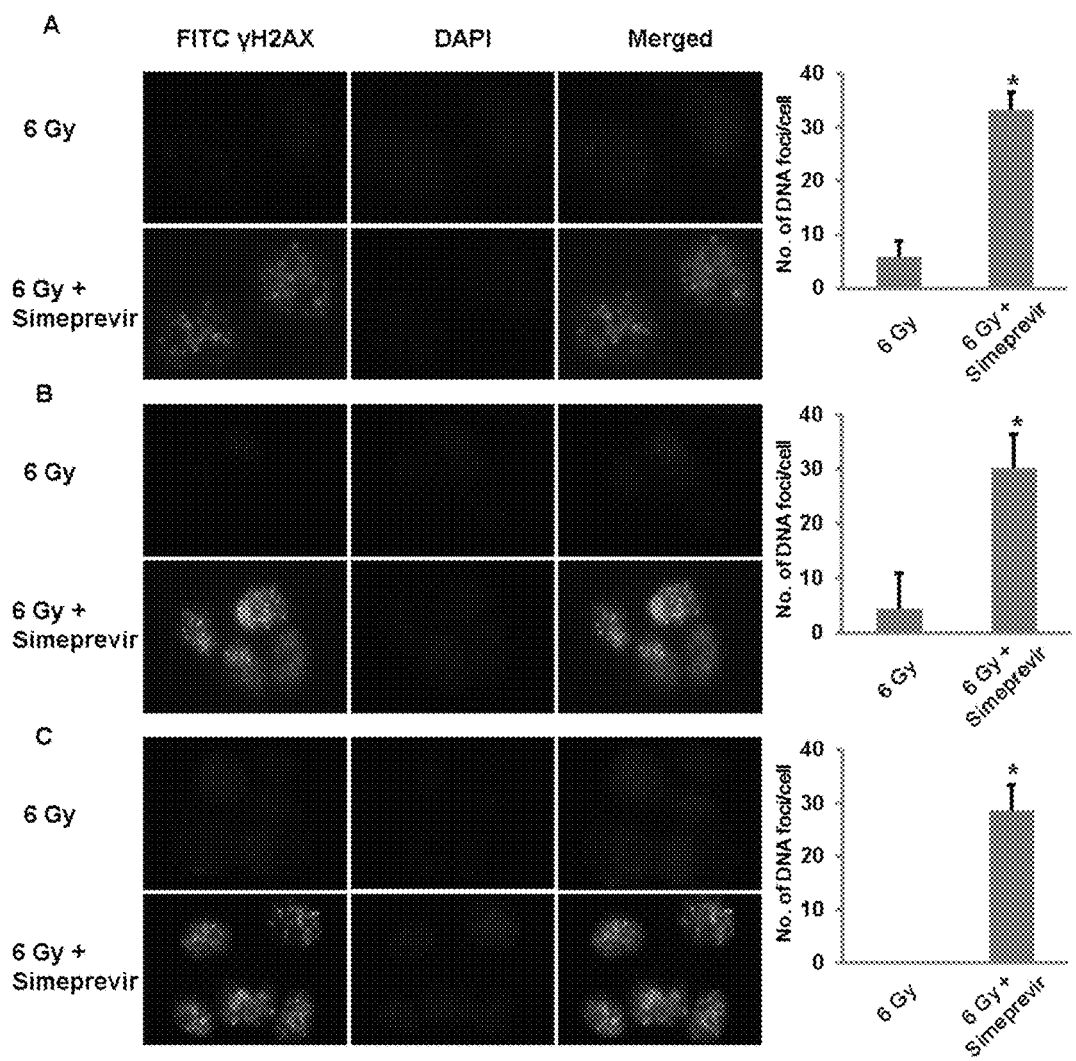
FIG. 8 is a diagram verifying an effect on DNA damage and repair mechanisms when inhibiting PI4K isozyme expression through γ-H2AX foci experiment.

In order to verify an effect of a simeprevir on DNA damage and repair mechanisms induced by radiation, a γ-H2AX foci experiment was performed by the same method as Experimental Example 3. The result was illustrated in FIG. 8.

Experimental Example 5. Verification of Radiation Sensitivity Enhancement Effect by Antiviral Agents in Tumor Xenograft Model In Vivo In order to form a tumor xenograft model in vivo, 5×106 human breast cancer cell lines BT-474 were injected to a hind leg of a BALB/c athymic nude mouse. After 3 weeks, it was verified that the tumor was uniformly grown, and the mouse was randomly assigned to four groups of a control group, a simeprevir group, a radiation irradiation group, and a simeprevir+radiation irradiation group. The simeprevir was administered to peritoneal cavity with a concentration of 10 mg/Kg three times a week for two weeks, and the radiation was irradiated with 9 Gy three times a week by 3 Gy by electron beam of 6 MeV while covering 1 cm bolus. After the entire treatment was finished, the size of the tumor was measured at an interval of about 1 week, and the result was illustrated in FIG. 9.

Figure 9:
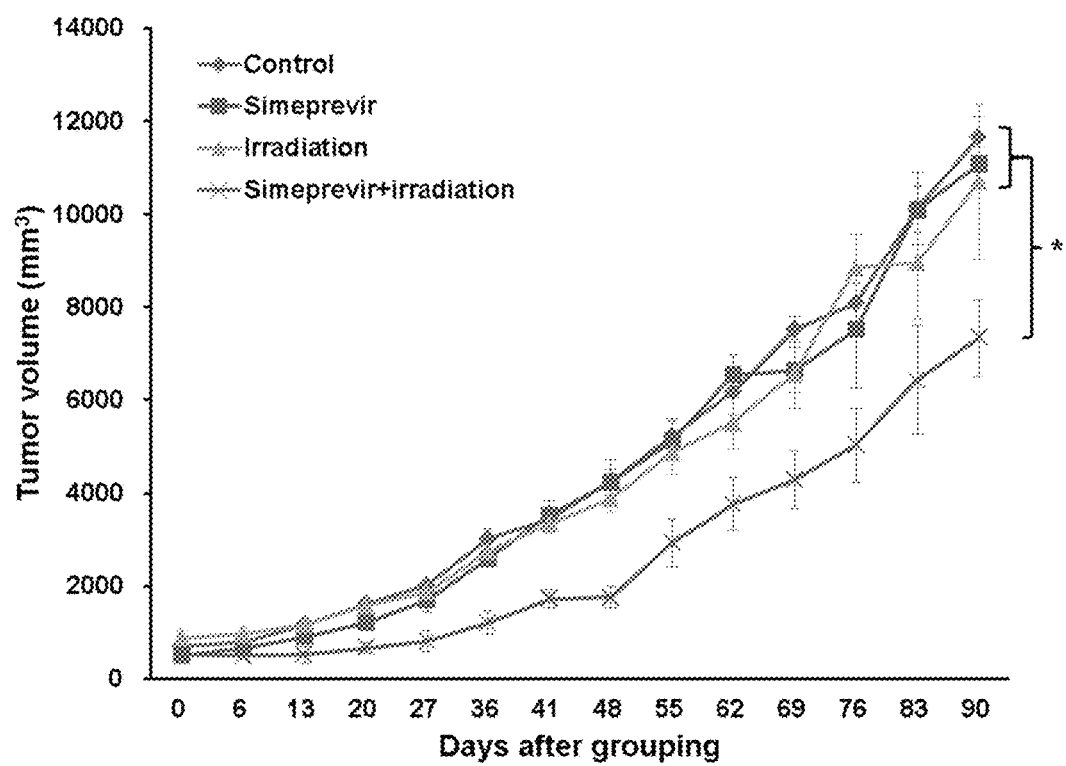
FIG. 9 is a diagram verifying a change in size of a tumor after administrating simeprevir and irradiating radiation to tumor xenograft mice in vivo.

As illustrated in FIG. 9, in the case of the simeprevir and radiation irradiation group, as compared with other groups, it was observed that the growth of the tumor was significantly inhibited. As a result, in the tumor xenograft model in vivo, it was verified that the sensitivity to radiation was enhanced by the simeprevir treatment.

Hereinafter, Preparation Examples of the pharmaceutical composition and the food composition will be described, but the present disclosure is not limited thereto but will be described in detail.

Preparation Example 1. Preparation of Pharmaceutical Composition 1-1. Preparation of Powder

| | |
|---|---|
| PI4K isozyme-specific siRNA or antiviral agent | 20 mg |
| Lactose | 100 mg |
| Talc | 10 mg |

The ingredients were mixed and packed in an airtight bag to prepare the powder.

1-2. Preparation of Tablet

| | |
|---|---|
| PI4K isozyme-specific siRNA or antiviral agent | 10 mg |
| Corn starch | 100 mg |
| Lactose | 100 mg |
| Magnesium stearate | 2 mg |

The ingredients were mixed and tableted according to a general tablet preparing method to prepare the tablet.

1-3. Preparation of Capsule

| | |
|---|---|
| PI4K isozyme-specific siRNA or antiviral agent | 10 mg |
| Crystalline cellulose | 3 mg |
| Lactose | 14.8 mg |
| Magnesium stearate | 0.2 mg |

The ingredients were mixed and filled in a gelatin capsule according to a general capsule preparing method to prepare the capsule.

1-4. Preparation of Injection

| | |
|---|---|
| PI4K isozyme-specific siRNA or antiviral agent | 10 mg |
| Mannitol | 180 mg |
| Sterile distilled water for injection | 2974 mg |
| $Na_2HPO_4 2H_2O$ | 26 mg |

The injection was prepared with the content of ingredients per 1 ampoule (2 ml) according to a general method of preparing the injection.

1-5. Preparation of Solution

| | |
|---|---|
| PI4K isozyme-specific siRNA or antiviral agent | 20 mg |
| Isomerized glucose | 10 g |
| Mannitol | 5 g |
| Purified water | suitable amount |

According to a general preparing method of the solution, respective ingredients were added in purified water and dissolved, added with a suitable amount of lemon flavoring, and mixed and then added with purified water so as to be adjusted to the entire 100 ml, and then filled in a dark amber bottle and sterilized to prepare the solution.

Preparation Example 2. Preparation of Food Composition 2-1. Preparation of Health Food

| | |
|---|---|
| PI4K isozyme-specific siRNA or antiviral agent | 100 mg |
| Vitamin mixture | suitable amount |
| Vitamin A acetate | 70 g |
| Vitamin E | 1.0 mg |
| Vitamin B1 | 0.13 mg |
| Vitamin B2 | 0.15 mg |
| Vitamin B6 | 0.5 mg |
| Vitamin B12 | 0.2 g |
| Vitamin C | 10 mg |
| Biotin | 10 g |
| Nicotinamide | 1.7 mg |
| Folic acid | 50 g |
| Calcium pantothenate | 0.5 mg |
| Mineral mixture | suitable amount |
| Ferrous sulfate | 1.75 mg |
| Zinc oxide | 0.82 mg |
| Magnesium carbonate | 25.3 mg |
| First potassium phosphate | 15 mg |
| Second potassium phosphate | 55 mg |
| Potassium citrate | 90 mg |
| Calcium carbonate | 100 mg |
| Magnesium chloride | 24.8 mg |

A composition ratio of the mixture of vitamins and mineral was set by mixing ingredients relatively suitable for a health food, but a mixed ratio may be randomly modified. According to a general method of preparing the health food, the ingredients were mixed to prepare granules and may be used for preparing the health food composition according to a general method.

2-2. Preparation of Health Beverage

| | |
|---|---|
| PI4K isozyme-specific siRNA or antiviral agent | 100 mg |
| Vitamin C | 15 g |
| Vitamin E (powder) | 100 g |
| Iron lactate | 19.75 g |
| Zinc oxide | 3.5 g |
| Nicotinamide | 3.5 g |
| Vitamin A | 0.2 g |
| Vitamin B1 | 0.25 g |
| Vitamin B2 | 0.3 g |
| Water | required amount |

According to a general method of preparing health beverages, the ingredients were mixed, stirred and heated for about 1 hour at 85° C., a prepared solution was filtrated to be obtained in a sterilized container of 2 L, sterilized after sealing, and refrigerated, and then used for preparing the health beverage composition of the present disclosure.

The composition ratio was set by mixing ingredients relatively suitable for a favorite beverage, but a mixed ratio may be randomly modified and implemented according to regional and national preference such as demand layers, demand countries, and a purpose of use.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A method for enhancing radiation sensitivity to radiotherapy, the method comprising administering a PI4K inhibiting hepatitis C virus treating agent to a subject undergoing radiotherapy.

2. The method of claim 1, wherein the PI4K inhibiting hepatitis C virus treating agent is at least one selected from the group consisting of simeprevir and sofosbuvir.

3. The method of claim 2, wherein the PI4K inhibiting hepatitis C virus treating agent is simeprevir represented by the following Formula 1:

[Formula 1]

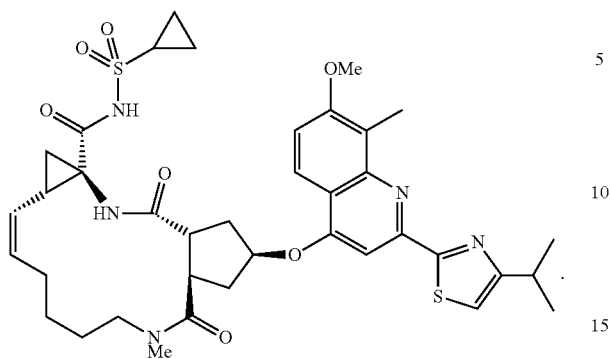

4. A method for assisting anticancer treatment in a subject having cancer and undergoing radiotherapy, the method comprising administering a PI4K inhibiting hepatitis C virus treating agent to the subject undergoing radiotherapy.

5. The method of claim 4, wherein the cancer is lung cancer, bone cancer, pancreatic cancer, skin cancer, oral cancer, pharynx cancer, uterine cancer, ovarian cancer, rectal cancer, stomach cancer, breast cancer, endometrial carcinoma, cervical carcinoma, vaginal carcinoma, small intestine cancer, thyroid cancer, parathyroid cancer, prostate cancer, chronic or acute leukemia, lymphocytic lymphoma, bladder cancer, kidney cancer, liver cancer, colon cancer, or brain tumor.

* * * * *

SEQUENCE LISTING

```
<160> NUMBER OF SEQ ID NOS: 16

<210> SEQ ID NO 1
<211> LENGTH: 19
<212> TYPE: RNA
<213> ORGANISM: Artificial Sequence
<220> FEATURE:
<223> OTHER INFORMATION: Description of Artificial Sequence: Synthetic
      PI4K-siRNA oligonucleotide

<400> SEQUENCE: 1
gcaucgggcu accaccaaa                                                  19

<210> SEQ ID NO 2
<211> LENGTH: 19
<212> TYPE: RNA
<213> ORGANISM: Artificial Sequence
<220> FEATURE:
<223> OTHER INFORMATION: Description of Artificial Sequence: Synthetic
      PI4K-siRNA oligonucleotide

<400> SEQUENCE: 2
gagacgagcc cacuagugu                                                  19

<210> SEQ ID NO 3
<211> LENGTH: 19
<212> TYPE: RNA
<213> ORGANISM: Artificial Sequence
<220> FEATURE:
<223> OTHER INFORMATION: Description of Artificial Sequence: Synthetic
      PI4K-siRNA oligonucleotide

<400> SEQUENCE: 3
caacacugau cgaggcaau                                                  19

<210> SEQ ID NO 4
<211> LENGTH: 19
<212> TYPE: RNA
<213> ORGANISM: Artificial Sequence
<220> FEATURE:
<223> OTHER INFORMATION: Description of Artificial Sequence: Synthetic
      PI4K-siRNA oligonucleotide

<400> SEQUENCE: 4
gguugguggu gcuggauua                                                  19

<210> SEQ ID NO 5
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      PI4K-siRNA oligonucleotide

<400> SEQUENCE: 5
gguaguaaau gucagagua                                                    19

<210> SEQ ID NO 6
<211> LENGTH: 19
<212> TYPE: RNA
<213> ORGANISM: Artificial Sequence
<220> FEATURE:
<223> OTHER INFORMATION: Description of Artificial Sequence: Synthetic
      PI4K-siRNA oligonucleotide

<400> SEQUENCE: 6
guuacaagga ggcugaaua                                                    19

<210> SEQ ID NO 7
<211> LENGTH: 19
<212> TYPE: RNA
<213> ORGANISM: Artificial Sequence
<220> FEATURE:
<223> OTHER INFORMATION: Description of Artificial Sequence: Synthetic
      PI4K-siRNA oligonucleotide

<400> SEQUENCE: 7
ucucaagguu caaguggaa                                                    19

<210> SEQ ID NO 8
<211> LENGTH: 19
<212> TYPE: RNA
<213> ORGANISM: Artificial Sequence
<220> FEATURE:
<223> OTHER INFORMATION: Description of Artificial Sequence: Synthetic
      PI4K-siRNA oligonucleotide

<400> SEQUENCE: 8
ugguuuggcu ugucaguga                                                    19

<210> SEQ ID NO 9
<211> LENGTH: 19
<212> TYPE: RNA
<213> ORGANISM: Artificial Sequence
<220> FEATURE:
<223> OTHER INFORMATION: Description of Artificial Sequence: Synthetic
      PI4K-siRNA oligonucleotide

<400> SEQUENCE: 9
ccuuuaagcu gaccacaga                                                    19

<210> SEQ ID NO 10
<211> LENGTH: 19
<212> TYPE: RNA
<213> ORGANISM: Artificial Sequence
<220> FEATURE:
<223> OTHER INFORMATION: Description of Artificial Sequence: Synthetic
      PI4K-siRNA oligonucleotide

<400> SEQUENCE: 10
ccgagaguau ugauaauuc                                                    19

<210> SEQ ID NO 11
<211> LENGTH: 19
<212> TYPE: RNA
<213> ORGANISM: Artificial Sequence
<220> FEATURE:
<223> OTHER INFORMATION: Description of Artificial Sequence: Synthetic
      PI4K-siRNA oligonucleotide
```

-continued

```
<400> SEQUENCE: 11
cccaguugcu uaacaugua                                                  19

<210> SEQ ID NO 12
<211> LENGTH: 19
<212> TYPE: RNA
<213> ORGANISM: Artificial Sequence
<220> FEATURE:
<223> OTHER INFORMATION: Description of Artificial Sequence: Synthetic
      PI4K-siRNA oligonucleotide

<400> SEQUENCE: 12
ggacucacca gcgcucuaa                                                  19

<210> SEQ ID NO 13
<211> LENGTH: 19
<212> TYPE: RNA
<213> ORGANISM: Artificial Sequence
<220> FEATURE:
<223> OTHER INFORMATION: Description of Artificial Sequence: Synthetic
      PI4K-siRNA oligonucleotide

<400> SEQUENCE: 13
gcuaugugcg ggaguauau                                                  19

<210> SEQ ID NO 14
<211> LENGTH: 19
<212> TYPE: RNA
<213> ORGANISM: Artificial Sequence
<220> FEATURE:
<223> OTHER INFORMATION: Description of Artificial Sequence: Synthetic
      PI4K-siRNA oligonucleotide

<400> SEQUENCE: 14
gaucgagcgu cucaucaca                                                  19

<210> SEQ ID NO 15
<211> LENGTH: 19
<212> TYPE: RNA
<213> ORGANISM: Artificial Sequence
<220> FEATURE:
<223> OTHER INFORMATION: Description of Artificial Sequence: Synthetic
      PI4K-siRNA oligonucleotide

<400> SEQUENCE: 15
guggccaacu ggagaucua                                                  19

<210> SEQ ID NO 16
<211> LENGTH: 19
<212> TYPE: RNA
<213> ORGANISM: Artificial Sequence
<220> FEATURE:
<223> OTHER INFORMATION: Description of Artificial Sequence: Synthetic
      PI4K-siRNA oligonucleotide

<400> SEQUENCE: 16
ggaacgaagu gacccgucu                                                  19
```